(12) United States Patent
Dave et al.

(10) Patent No.: US 7,591,824 B2
(45) Date of Patent: Sep. 22, 2009

(54) SURGICAL INSTRUMENT

(76) Inventors: Amar L. Dave, 1209 Starfire Dr., Suite 1, Ottawa, IL (US) 61350-1693; Roop K. Dave, 514 Avon La., Ottawa, IL (US) 61350

( * ) Notice: Subject to any disclaimer, the term of this patent is extended or adjusted under 35 U.S.C. 154(b) by 376 days.

(21) Appl. No.: 11/521,421

(22) Filed: Sep. 14, 2006

(65) Prior Publication Data

US 2007/0060928 A1    Mar. 15, 2007

Related U.S. Application Data

(60) Provisional application No. 60/717,435, filed on Sep. 15, 2005.

(51) Int. Cl.
*A61B 17/32* (2006.01)
(52) U.S. Cl. ..................................... 606/118
(58) Field of Classification Search ................. 606/118, 606/179
See application file for complete search history.

(56) References Cited

U.S. PATENT DOCUMENTS

| | | | |
|---|---|---|---|
| 1,417,142 A * | 5/1922 | Couch | 606/118 |
| 2,296,594 A | 9/1942 | Blais et al. | |
| 2,345,639 A | 4/1944 | Tibone et al. | |
| 2,471,864 A | 5/1949 | De Palo | |
| 3,056,407 A | 10/1962 | Kariher et al. | |
| 3,072,126 A | 1/1963 | Fenton | |
| 3,741,215 A * | 6/1973 | Ayad | 606/118 |
| 6,660,012 B2 * | 12/2003 | Lahiji | 606/118 |
| 7,303,567 B1 * | 12/2007 | Smith | 606/118 |
| 2002/0077642 A1 * | 6/2002 | Patel et al. | 606/167 |
| 2004/0215210 A1 * | 10/2004 | Duel | 606/118 |
| 2006/0122626 A1 * | 6/2006 | Duel | 606/118 |
| 2008/0004654 A1 * | 1/2008 | Tomlinson | 606/201 |

* cited by examiner

*Primary Examiner*—(Jackie) Tan-Uyen T Ho
*Assistant Examiner*—Alexander Orkin
(74) *Attorney, Agent, or Firm*—James Ray & Assoc.

(57) ABSTRACT

A surgical device for performing a circumcision includes a hollow body open at both ends thereof. A Y-shaped handle is positioned adjacent an anterior end of the body and has each leg secured to one of two diametrically opposed points on the anterior end. Each leg has a portion thereof disposed adjacent a juncture with the anterior end of the body being weaker than any other portion of the body, whereby a reciprocation of the handle causes the handle to fracture at each juncture and become detached from the body. A pair of pointed barbs are rigidly attached to a predetermined portion of the handle for positively retaining a distal portion of the foreskin. A plurality of pointed barbed serrations are formed adjacent the anterior end of the body for separating the distal portion of the foreskin. The handle has a rounded distal end for separating the foreskin from the glans.

20 Claims, 1 Drawing Sheet

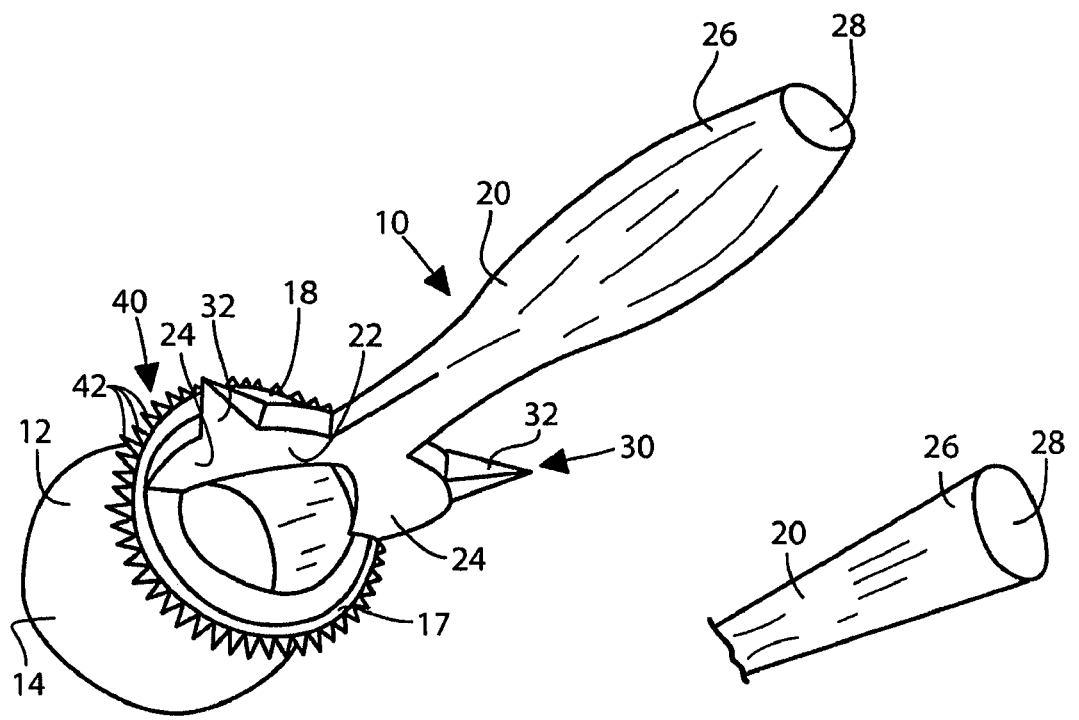
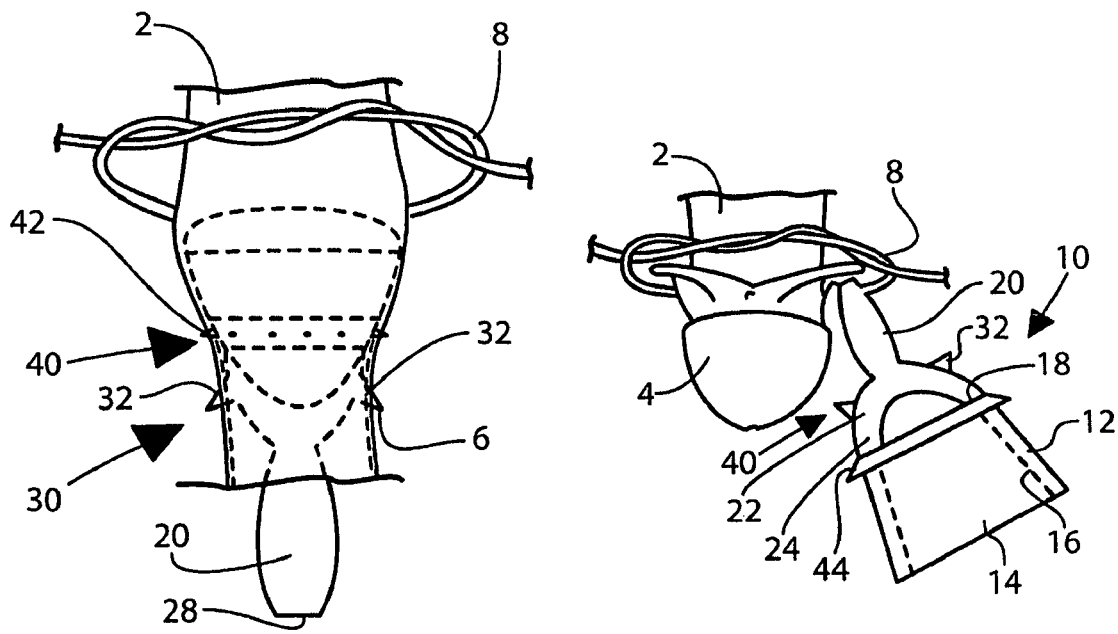

SURGICAL INSTRUMENT

CROSS-REFERENCE TO RELATED APPLICATIONS

This application is related to and claims priority from Provisional Patent Application Ser. No. 60/717,435 filed Sep. 15, 2005.

FIELD OF THE INVENTION

The present invention relates, in general, to surgical instruments and, more particularly, this invention relates to a surgical instrument for performing circumcisions.

BACKGROUND OF THE INVENTION

As is generally well known, a Plastibell method is often used to circumcise infant boys. In this method, an edge of the foreskin is first pulled open with clamps and a probe is inserted to tear the foreskin off the penile head. Next, if the size of the meatal opening is very small, a "Dorsal crush" is made to prevent bleeding and then cut and the ligature, such as string, is placed around the penis for later use. Then, as the foreskin is laid back exposing the glans, a Plastibell surgical instrument is inserted over the glans and the foreskin is pulled forward and over the bell shaped body portion of such instrument. Next, a clamp is placed to hold the foreskin to the Plastibell's Y-shaped handle and to maintain the Plastibell in its optimum position. The string is tied in the Plastibell's groove and the portion of the foreskin is cut off with scissors starting at the dorsal slit and using the anterior end of the body portion as a guide. Finally, the Plastibell's handle is snapped of at its juncture with the anterior end of the body portion to complete the procedure. The structure of the Plastibell is disclosed in U.S. Pat. No. 3,056,407 issued to Kariher et al.

Several problems are constantly encountered in using the existing Plastibell method. The first problem is encountered in that the foreskin may slip and retract during the procedure thus often leading to another circumcision or even to adhesion of the foreskin to the glans. The second problems is encountered in that the sterile forceps are required to hold the outer edge of the foreskin and sterile scissors or other cutting tools are required to cut off the foreskin portion. The need for multiple sterile instruments poses difficulties in certain geographical areas where sterilization procedures may be of less than desirable quality and proper instruments may not be available.

Therefore, there is a need for an improved surgical instrument for performing circumcisions.

SUMMARY OF THE INVENTION

According to one embodiment, the invention provides a surgical device for performing a circumcision. The device includes a hollow body which is open at both ends thereof. A Y-shaped handle is positioned adjacent an anterior end of the body and has each leg secured to one of two diametrically opposed points on the anterior end. Each leg has a portion thereof disposed adjacent a juncture with the anterior end of the body being weaker than any other portion of the body, whereby a reciprocation of the handle causes the handle to fracture at each juncture and become detached from the body. The device includes means which is rigidly attached to a predetermined portion of the handle for positively retaining a distal portion of the foreskin.

According to another embodiment of the invention, there is provided a surgical device for performing a circumcision. The device includes a hollow body which is open at both ends thereof. A Y-shaped handle is positioned adjacent an anterior end of the body and has each leg secured to one of two diametrically opposed points on the anterior end. Each leg has a portion thereof disposed adjacent a juncture with the anterior end of the body being weaker than any other portion of the body, whereby a reciprocation of the handle causes the handle to fracture at each juncture and become detached from the body. The device further includes means which is formed on the body for excising a distal portion of a foreskin.

According to yet another embodiment, the invention provides a method of performing a circumcision. The method includes the step of providing a surgical device having a hollow body which is open at both ends thereof, a Y-shaped handle positioned adjacent an anterior end of the body and having each leg thereof secured to one of two diametrically opposed points on the anterior end, the each leg having a portion thereof disposed adjacent a juncture with the anterior end of the body being weaker than any other portion of the body, and means engageable with the handle for positively retaining a distal portion of a foreskin. Then, loosely placing a ligature around a penis. Next, separating the foreskin from penile glans. Further, retracting the separated foreskin. Then, exposing the penile glans. Next, positioning the hollow body over the exposed penile glans. Pulling the foreskin over the hollow body and over a portion of the Y-shaped handle. Next, securing, by way of the foreskin retaining means, the distal portion of the foreskin to the handle. Then, securing, by way of the ligature, the foreskin to the hollow body of the surgical device. Cutting off the distal portion of the foreskin. Finally, detaching the Y-shaped handle from the hollow body.

According to a further embodiment of the invention, there is provided a method of performing a circumcision. The method includes the step of providing a surgical device having a hollow body open at both ends thereof, a Y-shaped handle positioned adjacent an anterior end of the body and having each leg thereof secured to one of two diametrically opposed points on the anterior end, the each leg having a portion thereof disposed adjacent a juncture with the anterior end of the body being weaker than any other portion of the body, and means which is formed on the exterior surface of the body excising a distal portion of a foreskin. Then, loosely placing a ligature around a penis. Next, separating the foreskin from penile glans. Further, retracting the separated foreskin. Then, exposing the penile glans. Next, positioning the hollow body over the exposed penile glans. Pulling the foreskin over the hollow body and over a portion of the Y-shaped handle. Then, securing the distal portion of the foreskin to the handle. Next, securing, by way of the ligature, the foreskin to the hollow body of the instrument. The method further includes the step of cutting off, by way of the foreskin excising means, the distal portion of the foreskin. Finally, detaching the Y-shaped handle from the body.

OBJECTS OF THE INVENTION

It is, therefore, one of the primary objects of the present invention to provide a surgical instrument for performing circumcisions.

Another object of the present invention is to provide a surgical instrument for performing circumcisions which does not require use of sterile forceps and clamps to hold foreskin during the circumcision procedure.

Yet another object of the present invention is to provide a surgical instrument for performing circumcisions which does not require use of sterile scissors or other cutting tools.

A further object of the present invention is to provide a surgical instrument for performing circumcisions which eliminates slippage and retraction of the foreskin.

Yet a further object of the present invention is to provide a surgical instrument for performing circumcisions which is capable of anchoring a distal portion of the foreskin to be excised during the circumcision procedure.

An additional object of the present invention is to provide a surgical instrument for performing circumcisions which is economical to manufacture.

Another object of the present invention is to provide a surgical instrument for performing circumcisions which is simple to use.

In addition to the several objects and advantages of the present invention which have been described with some degree of specificity above, various other objects and advantages of the invention will become more readily apparent to those persons who are skilled in the relevant art, particularly, when such description is taken in conjunction with the attached drawing Figures and with the appended claims.

BRIEF DESCRIPTION OF THE DRAWINGS

FIG. 1 is a perspective view of a surgical instrument of the present invention for performing circumcisions;

FIG. 2 is a is partial perspective view of the surgical instrument of the present invention, particularly illustrating an alternative handle construction;

FIG. 3 is a side view of the surgical instrument being applied during the circumcision procedure to separate foreskin from the glans; and FIG. 4 is a side view of the surgical instrument being applied during the circumcision procedure to retain and separate the foreskin.

BRIEF DESCRIPTION OF THE VARIOUS EMBODIMENTS OF THE INVENTION

Prior to proceeding to the more detailed description of the present invention, it should be noted that, for the sake of clarity and understanding, identical components which have identical functions have been identified with identical reference numerals throughout the several views illustrated in the drawing figures.

Reference is now made, to FIGS. 1-4, wherein there is shown a surgical device, generally designated as 10, for performing a circumcision. The construction of the surgical device 10 is similar to the surgical device taught in U.S. Pat. No. 3,056,407 issued Oct. 2, 1962 to Kariher et al and the disclosure of U.S. Pat. No. 3,056,407 is incorporated into this document by reference thereto.

The surgical device 10 includes a hollow body 12 which is open at both ends thereof. The body 12 includes an interior surface 16 thereof being conically shaped and tapered to define an enlarged opening at a posterior end 14 of the body 12. As it is well known, the device 10 includes an annular flange 17 which is secured to an exterior surface of the body 12 adjacent the anterior end 18 thereof.

A Y-shaped handle 20 is positioned adjacent the anterior end 18 of the body 12 and has each leg 22 thereof secured to one of two diametrically opposed points on the anterior end 18. Each leg 22 has a portion 24 thereof disposed adjacent a juncture with the anterior end 18 of the body 12 being weaker than any other portion of the body 12. Such construction enables slight reciprocation of the handle 20 to cause the handle 20 to fracture at each juncture and become detached from the body 12. Such portion 24 of each leg 22 which is disposed adjacent the juncture with the anterior end 18 of the body 12 is further being thinner than any other portion of the handle 20. Preferably, the handle 20 has a portion 26 which has a frustoconical shape and which tapers toward the distal closed end 28 of the handle 20, as best shown in FIG. 1. Alternatively, the portion 26 of the handle 20 tapers from a distal round end 28 toward the anterior end 18 of the body 12, as best shown in FIG. 2. The round shape of the distal end 28 has been found to be advantageous in separating the foreskin 6 from the glans 4 of the penis 2.

According to one embodiment of the invention, the surgical device 10 includes means, generally designated as 30, which is rigidly attached to a predetermined portion of the handle 20 for positively retaining a distal portion of the foreskin 6. In the presently preferred embodiment of the invention, such foreskin retaining means 30 includes a pair of pointed barbs 32, each rigidly attached to a respective leg 22 of the handle 20 and pointed at a predetermined angle to a longitudinal axis of the handle 20 away from the anterior end 18 of the hollow body 12. In use, each pointed barb 32 is capable of puncturing a wall of the foreskin 6. It has been found that use of pointed barbs 32 eliminates slippage and retraction of the foreskin 6 during the circumcision procedure.

In use, the ligature 8 is loosely placed around the penis 2 and the foreskin 6 is separated from the glans 4 either using the distal end 28 of the handle 20, as best shown in FIG. 3, or by any other conventional means. The foreskin 6 is than retracted toward the scrotum (not shown) to expose the penile glans 4. The body 12 is positioned over the exposed glans 4 and the foreskin 6 is pulled over the body 12 and over a portion of the Y-shaped handle 20. A well known dorsal crush and slit may be performed prior to positioning the body 12 over the glans 4 if the meatal opening is too small. Next, the distal portion of the foreskin 6 is secured by way of the barbs 32 puncturing the wall of the foreskin 6 and anchoring it thereonto, as best shown in FIG. 4. Then, in a conventional fashion, the ligature 8 is tied adjacent the flange 17 to secure the foreskin 6 to the hollow body 12 and the distal portion of the foreskin 6 is cut-off. Finally, the handle 20 is detached from the body 12.

According to another embodiment, the invention provides means, generally designated as 40, which is attached to the exterior surface of the body 12 for excising the distal portion of the foreskin 6. In the presently preferred embodiment of the invention, the foreskin excising means 40 includes a plurality of pointed barbed serrations 42 which are attached to the exterior surface of the body 12 in an annular fashion. Preferably, the serrations 42 are formed integral with the annular flange 17. Alternatively, each serration 42 may include a straight portion (not shown) which extends from the exterior surface of the body 12 for use in securing the foreskin 6 with the ligature 8. The height of each serration 42 is formed sufficient to puncture the wall of the foreskin 6.

Yet alternatively, the foreskin excising means 40 includes a knife-like annular flange 44 which is positioned adjacent the anterior end 18 of the body 12, as best shown in FIG. 3.

In use, the ligature 8 is loosely placed around the penis 2 and the foreskin 6 is separated from the glans 4 either using the distal end 28 of the handle 20, as best shown in FIG. 3, or by any other conventional means. The foreskin 6 is than retracted toward the scrotum (not shown) to expose the penile glans 4. The body 12 is positioned over the exposed glans 4 and the foreskin is pulled over the hollow body 12 and over a portion of the Y-shaped handle 20. Next, the distal portion of the foreskin 6 is secured either by way of the barbs 32 puncturing the wall of the foreskin 6 and anchoring the foreskin 6 thereonto, or by using the clamp (not shown) in a conventional fashion. Then, the ligature 8 is tied adjacent the flange 17 to secure the foreskin 6 to the hollow body 12 and the distal portion of the foreskin 6 is separated by way of the barbed serrations 42 or the knife-like edge 44. Finally, the handle 20 is detached from the body 12.

It will be understood by those skilled in the relevant art form that the surgical device 10 including both the foreskin retaining means 30 and the foreskin excising means 40 does not require use of sterile forceps and clamps to hold foreskin 6 during the circumcision procedure and does not require use of sterile scissors or other cutting tools to excise the distal portion of the foreskin 6.

The surgical device 10 is preferably formed as a unitary member from a clear plastic material.

Thus, the present invention has been described in such full, clear, concise and exact terms as to enable any person skilled in the art to which it pertains to make and use the same. It will be understood that variations, modifications, equivalents and substitutions for components of the specifically described embodiments of the invention may be made by those skilled in the art without departing from the spirit and scope of the invention as set forth in the appended claims.

We claim:

1. A surgical device for performing a circumcision, said device comprising:
   (a) a hollow body open at both ends thereof;
   (b) a Y-shaped handle having an elongated member and a pair of legs disposed on a proximate end of said elongated member and positioned adjacent an anterior end of said body each leg having distal end thereof secured to one of two diametrically opposed points on said anterior end, said each leg having a portion thereof disposed adjacent a juncture with said anterior end of said body being weaker than any other portion of said body, whereby a reciprocation of said handle causes said handle to fracture at each juncture and become detached from said body; and
   (c) a pair of barbs, each of said pair of barbs disposed stationary on and extending outwardly from an exterior curved edge of a respective leg, said each barb having each of a proximate end thereof rigidly positioned on said exterior curved edge, a pointed distal end thereof spaced from said curved edge and a plurality of triangular shaped side surfaces connecting said pointed distal end with said proximate end, wherein said each of said pair of barbs is pointed at a predetermined angle relative to a longitudinal axis of said elongated member away from said anterior end of said hollow body, and wherein a height of said each of said pair of pointed barbs is sufficient to puncture a wall of a foreskin.

2. The surgical device, according to claim 1, wherein said body includes an interior surface thereof being conically shaped and tapered to define an enlarged opening at a posterior end of said body.

3. The surgical device, according to claim 1, wherein a distal end of said elongated member of said handle has each of a round shape a and planar surface for aiding in separating said foreskin from penile glans.

4. The surgical device, according to claim 1, wherein said elongated member of said handle tapers from a distal end thereof toward said anterior end of said body.

5. The surgical device, according to claim 1, wherein a portion of said elongated member of said handle disposed adjacent a distal end thereof has a frustoconical shape.

6. The surgical device, according to claim 1, wherein said portion of said each leg disposed adjacent said juncture with said anterior end of said body is being thinner than any other portion of said handle.

7. The surgical device, according to claim 1, wherein said device includes an annular ring secured to an exterior surface of said body adjacent said anterior end thereof.

8. The surgical device, according to claim 1, wherein said device further includes means attached to an exterior surface of said body for excising said distal portion of said foreskin.

9. The surgical device, according to claim 8, wherein said foreskin excising means includes an annular flange positioned adjacent said anterior end of said body and a plurality of outwardly extending pointed barbs disposed, in a plane transverse to said longitudinal axis of said elongated member, on an outer edge of said annular ring.

10. The surgical device, according to claim 9, wherein said plurality of pointed barbs are formed integral with said annular flange.

11. The surgical device, according to claim 9, wherein said plurality of pointed barbs are formed integral with said exterior surface of said body.

12. The surgical device, according to claim 8, wherein said foreskin excising means includes a knife-like annular flange positioned on said exterior surface of said body adjacent said anterior end thereof, said knife-like annular flange having a peripheral edge thereof tapering inwardly toward said anterior end of said body.

13. The surgical device, according to claim 1, wherein a material of said device is a clear plastic.

14. The surgical device, according to claim 1, wherein said device is formed as a unitary member from a plastic material.

15. A surgical device for performing a circumcision, said device comprising:
   (a) a hollow body open at both ends thereof;
   (b) a Y-shaped handle having an elongated member and a pair of legs disposed on a proximate end of said elongated member and positioned adjacent an anterior end of said body each leg having distal end thereof secured to one of two diametrically opposed points on said anterior end, said each leg having a portion thereof disposed adjacent a juncture with said anterior end of said body being weaker than any other portion of said body, whereby a reciprocation of said handle causes said handle to fracture at each juncture and become detached from said body and wherein a portion of said elongated member of said handle disposed adjacent a distal end thereof has a frustoconical shape tapering toward said distal end; and
   (c) a plurality of pointed barbs disposed, in an annular arrangement and in a plane substantially transverse to a longitudinal axis of said elongated member, on an exterior surface of said body and extending outwardly thereof.

16. The surgical device, according to claim 15, wherein said device includes means rigidly attached to a predetermined portion of said handle for positively retaining a portion of foreskin.

17. A method of performing a circumcision, said method comprising the steps of:
   (a) providing a surgical device having a hollow body open at both ends thereof, a Y-shaped handle having a elongated member and a pair of legs disposed on a proximate end of said elongated member and positioned adjacent an anterior end of said body each leg having distal end thereof secured to one of two diametrically opposed points on said anterior end, said each leg having a portion thereof disposed adjacent a juncture with said anterior end of said body being weaker than any other portion of said body, and a pair of barbs, each of said pair of barbs disposed stationary on and extending outwardly from an exterior curved edge of a respective leg of said handle and having each of a proximate end thereof rigidly positioned on said exterior curved edge, a pointed distal end thereof spaced from said curved edge and a plurality of triangular shaped side surfaces connecting said pointed distal end with said proximate end, wherein said each of said pair of barbs is pointed at a predetermined angle relative to a longitudinal axis of said elongated member away from said anterior end of said hollow body, and wherein a height of said each of said pair of barbs is sufficient to puncture a wall of said foreskin;

(b) loosely placing a ligature around a penis;
(c) separating said foreskin from penile glans;
(d) retracting said foreskin separated in step (c);
(e) exposing said penile glans;
(f) positioning said hollow body over said penile glans exposed in step (e);
(g) pulling said foreskin over said hollow body and over a portion of said Y-shaped handle;
(h) securing, by way of said pair of barbs, said distal portion of said foreskin to said handle;
(i) securing, by way of said ligature positioned in step (b), said foreskin to said hollow body of said surgical device;
(j) cutting off said distal portion of said foreskin; and
(k) detaching said Y-shaped handle from said hollow body.

18. The method, according to claim 17, wherein said foreskin is separated from said glans in step (c) by way of a round distal end formed in said elongated member of said Y-shaped handle.

19. A method of performing a circumcision, said method comprising the steps of:

(a) providing a surgical device having a hollow body open at both ends thereof, a Y-shaped handle having an elongated member and a pair of legs disposed on a proximate end of said elongated member and positioned adjacent an anterior end of said body each leg having distal end thereof secured to one of two diametrically opposed points on said anterior end, said each leg having a portion thereof disposed adjacent a juncture with said anterior end of said body being weaker than any other portion of said body, an annular flange positioned on exterior surface of said body adjacent said anterior end thereof, and a plurality of outwardly extending pointed barbs disposed, in a plane transverse to a longitudinal axis of said elongated member, on an outer edge of said annular ring;
(b) loosely placing a ligature around a penis;
(c) separating said foreskin from penile glans;
(d) retracting said foreskin separated in step (c);
(e) exposing said penile glans;
(f) positioning said hollow body over said penile glans exposed in step (e);
(g) pulling said foreskin over said hollow body and over a portion of said Y-shaped handle;
(h) securing a distal portion of said foreskin to said handle;
(i) securing, by way of said ligature positioned in step (b), said foreskin to said hollow body of said instrument;
(j) cutting off, by way of said plurality of outwardly extending pointed barbs, said distal portion of said foreskin; and
(k) detaching said Y-shaped handle from said body.

20. The surgical device, according to claim 1, wherein a portion of said elongated member of said handle disposed adjacent a distal end thereof has a frustoconical shape tapering toward said distal end.

* * * * *